United States Patent [19]

Gambale et al.

[11] Patent Number: 4,922,924
[45] Date of Patent: May 8, 1990

[54] CATHETER GUIDEWIRE WITH VARYING RADIOPACITY

[75] Inventors: Richard A. Gambale, Tyngsboro, Mass.; James F. Crittenden, Hollis, N.H.

[73] Assignee: C. R. Bard, Inc., Murray Hill, N.J.

[21] Appl. No.: 344,018

[22] Filed: Apr. 27, 1989

[51] Int. Cl.⁵ .............................................. A61B 5/00
[52] U.S. Cl. ................................... 128/772; 128/657; 604/164; 604/280
[58] Field of Search ................ 128/657, 772; 604/164, 604/170, 280, 282

[56] References Cited

U.S. PATENT DOCUMENTS

| | | | |
|---|---|---|---|
| 3,731,671 | 5/1973 | Mageoh | 128/772 |
| 3,749,085 | 7/1973 | Willson et al. | 128/757 |
| 3,749,086 | 7/1973 | Kline et al. | 128/772 |
| 3,789,841 | 2/1974 | Antoshkiw | 128/772 |
| 4,003,369 | 1/1977 | Heilman et al. | 128/772 |
| 4,020,829 | 5/1977 | Willson et al. | 128/772 |
| 4,080,706 | 3/1978 | Heilman et al. | 128/772 |
| 4,215,703 | 8/1980 | Willson | 128/772 |
| 4,538,622 | 9/1985 | Samson et al. | 128/657 |
| 4,545,390 | 10/1985 | Leary | 128/772 |
| 4,554,929 | 11/1985 | Samson | 128/772 |
| 4,619,274 | 10/1986 | Morrison | 128/772 |
| 4,748,986 | 6/1988 | Morrison et al. | 128/772 |
| 4,763,647 | 8/1988 | Gambale | 128/772 |
| 4,773,432 | 9/1988 | Rydell | 128/772 |

Primary Examiner—Max Hindenburg
Assistant Examiner—Randy Shay
Attorney, Agent, or Firm—Wolf, Greenfield & Sacks

[57] ABSTRACT

A guidewire for use with a catheter has segments of varying radiopacity. The guidewire includes a coil assembly at its distal end, the coil assembly being formed from a highly radiopaque coil and a non-radiopaque coil, arranged in bifilar arrangement to define a moderate radiopacity section in which the radiopaque and non-radiopaque segment alternate and a highly radiopaque section composed solely of the highly radiopaque coil.

7 Claims, 1 Drawing Sheet

CATHETER GUIDEWIRE WITH VARYING RADIOPACITY

FIELD OF THE INVENTION

The invention relates to guidewires used to support and guide catheters as they are advanced through body lumens such as blood vessels.

BACKGROUND OF THE INVENTION

A wide variety of guidewires are used for various medical purposes in the treatment of the human body. Among the more common uses is in blood vessels to guide a catheter to a site within the patient's blood vessel to perform the procedure for which the catheter is adapted. For example, guidewires, particularly small diameter steerable guidewires perform an important function in percutaneous transluminal coronary angioplasty. Illustrative of such guidewires are those described in U.S. Pat. No. 4,545,390 (Leary) and U.S. Pat. No. 4,538,622 (Samson). Each of the guidewires described in those patents has a torsionally rigid, longitudinally flexible shaft and a flexible distal end that includes a coil, all or part of which is radiopaque so that the physician can monitor fluoroscopically the position and advancement of the guidewire in the patient's blood vessel. In procedures, such as coronary angioplasty, in which a catheter is advanced through the patient's arteries, it often is the practice to inject a radiopaque contrast liquid into the artery so that the shape and path of the artery may be visualized fluoroscopically. The radiopacity of the guidewire coil may be so dense as to visually obstruct part of the artery which the physician may desire to view when the contrast liquid is injected. For use in such instances, it would be desirable for the guidewire to be only partially radiopaque, that is, to form a light but visible grey shadow in some portions and a heavy, dark fluoroscopic image on another.

It also is desirable in the design of guidewires to coat the coil with a low friction material so as to reduce friction between the guidewire and catheter.

It is among the general object of the invention to provide guidewires having the foregoing desirable characteristics.

SUMMARY OF THE INVENTION

A guidewire, in accordance with the invention, has an elongate flexible shaft having a tapered distal portion. A helical coil formed from a radiopaque metal is mounted on the distal end of the shaft over the tapered portion, the tapered portion being received in and extending through the coil. The coil is formed from two elements, including a first coil formed from a highly radiopaque metal and a second, shorter coil that is formed from a flexible non-radiopaque polymeric material. The polymeric, plastic, non-radiopaque portion is wound together with the proximal end of the radiopaque coil so as to define a bifilar proximal coil segment characterized by alternating highly radiopaque and non-radiopaque coils. The portion of the coil that extends beyond the distal end of the plastic coil is entirely highly radiopaque and presents a darker image on the fluoroscope. Thus, the guidewire provides a distal coil having a highly radiopaque distal segment and a moderately radiopaque proximal segment which will not completely obstruct visualization of arteries into which radiopaque contrast liquid has been injected.

In another aspect of the invention, the frictional characteristics of the coil are reduced by making the plastic coil a slightly larger diameter than the highly radiopaque coil. With that configuration, the proximal portion of the coil assembly presents fewer and smaller areas of contact with the catheter and thereby lowers friction with the catheter.

It is among the objects of the invention to provide a guidewire having a coil assembly at its distal end in which the coil assembly includes a highly radiopaque distal segment and a moderately radiopaque proximal segment.

Another object of the invention is to provide a guidewire having a coil assembly at its distal end in which the coil is formed from metal and non-metal elements.

A further object of the invention is to provide a guidewire having a coil assembly at its distal end in which the coil assembly is adapted to provide low friction characteristics with respect to the catheter in which it is used.

DESCRIPTION OF THE DRAWINGS

The foregoing and other objects and advantages of the invention will be appreciated more fully from the following further description thereof, with reference to the accompanying drawings wherein.

DESCRIPTION OF THE ILLUSTRATIVE EMBODIMENTS

Figure 1:
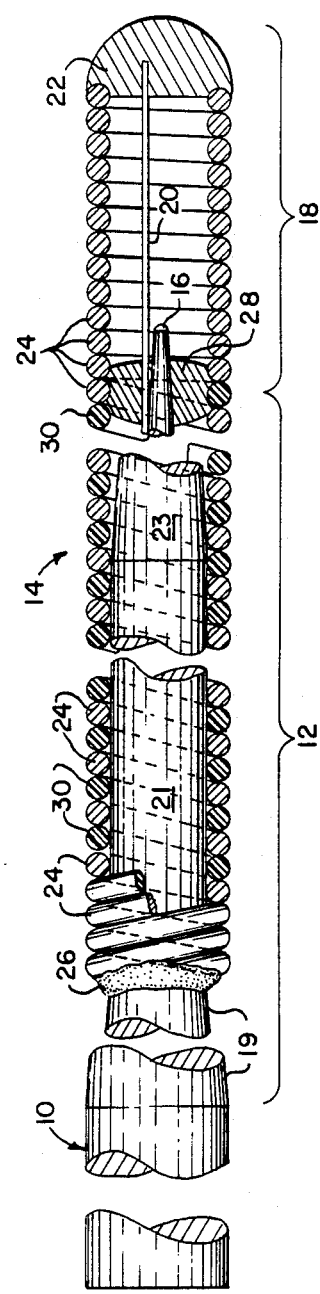
FIG. 1 is a longitudinal sectional, fragmented illustration of one embodiment of the invention.

As illustrated in FIG. 1, the guidewire includes an elongated rotationally rigid, longitudinally flexible shaft 10 having a tapered region 12 at its distal end. A coil assembly 14 is mounted to the distal end of the shaft 10, the tapered region 12 of the shaft 10 extending into and being received within the coil assembly 14. The distal tip 16 of the shaft 10 may terminate short of the distal end of the coil assembly 14 to define a flexible tip portion 18. A slender shaping wire or ribbon 20 may extend from the distal end of the shaft 10 to a tip weld 22 at the distal tip of the coil assembly. The overall length of the guidewire may be of the order of 175 cm, with tapered region 12 being approximately 30 cm long and tip portion 18 being approximately 2 cm long. The proximal portion of the shaft 10 may be of a diameter of between about 0.012" to about 0.016". The tapered region 12 may include a tapered segment 19, about 3 cm long, that tapers to a barrel segment 21 having a diameter of about 0.008"–0.010". Barrel segment 21 may be of the order of 24 cm long. The distal end of tapered region 12 may be tapered over the last approximately 6 cm to a distal diameter of approximately 0.002". The ribbon 20 may be formed from stainless steel and may be rectangular in cross-section, for example, 0.001" by 0.003".

In accordance with the invention, the coil assembly is formed from a first coil 24 which extends the full length of the coil assembly formed from a highly radiopague material such as a platinum tungsten alloy. The coil 24 preferably is formed from wire of the order of 0.003" diameter and is wound to define an outer diameter of about 0.014" to about 0.016". The coil 24 is attached to the shaft 10 at a proximal adhesive joint 26 and also at a distal brazed joint 28. A shorter helical coil 30 formed from a non-radiopague material, such as an appropriate flexible plastic, polymeric material (for example, polypropylene) is interposed among the coils of the first coil 24 along a proximal portion of the first coil 24 in a bifilar arrangement in which the turns of the first and second coils 24, 30 alternate. The second coil also may be formed from 0.003" diameter filament wound to the same outer diameter as the first coil 24. Both the first and second coils 24, 30 may be wound in a bifilar arrangement on a common mandrel. After winding, the polymeric material may be heated to enable it to become set in its wound helical configuration.

Thus, the coil assembly may be considered as having a distal section in which the highly radiopague turns of the coil 24 are adjacent each other and a proximal section in which the turns of the highly radiopague coil 24 are alternated with the non-radiopague turn of the second coil 30. Because the radiopague coil turns are spaced from each other in the proximal section, that section of the coil assembly will appear less dark on the fluoroscope. Thus, when viewed on a fluoroscope, the guidewire will exhibit a heavy dark distal portion and a moderately shadowed proximal portion. The moderately shadowed proximal portion permits visualization of the portion of the blood vessel in which it is contained when the blood vessel is injected with radiopague contrast liquid.

Figure 2:
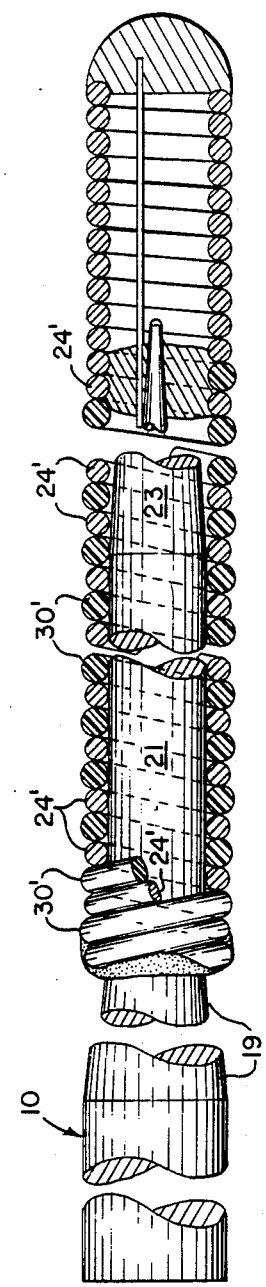
FIG. 2 is a longitudinal sectional, fragmented illustration of another embodiment of the invention.

FIG. 2 illustrates an embodiment similar to FIG. 1 but in which the second, plastic coil 30' is of a diameter slightly larger than the first coil 24'. For example, with the first coil 24' being formed from 0.003" diameter wire, the second coil 30' may be formed from filaments having a diameter of the order of 0.0032". Additionally, the plastic coil preferably is formed from a material having a relatively low coefficient of friction, such as polypropylene or polytetrafluoroethylene (Teflon). The guidewire having such construction will present less contact area with the inner surface of the catheter into which the guidewire is inserted and, therefore, will present less friction and better, more responsive feel for the physician.

Thus, I have described a guidewire having varied degrees of radiopacity and a configuration by which friction with the catheter is reduced. It should be understood, however, that the foregoing description of the invention is intended merely to be illustrative thereof and that other embodiments and modifications may be apparent to those skilled in the art without departing from its objectives, purposes and spirit.

Having thus described the invention what I desire to claim and secure by letters patent is:

1. A guidewire comprising:
    an elongate flexible shaft;
    a flexible coil assembly on the distal end of the shaft, the coil assembly being formed from a first coil formed from a highly radiopague material which extends the full length of the coil assembly and a second substantially non-radiopaque coil, shorter than the first coil, and interposed in bifilar configuration between some of the turns of the first coil to define a less radiopague segment of the coil assembly.

2. A guidewire as defined in claim 1 wherein the less radiopague segment is located at the proximal end of the coil assembly.

3. A guidewire as defined in claim 2 further comprising:
    the proximal end of the first and second coils being adhesively connected to each other and to the shaft.

4. A guidewire as defined in any of claims 1-3 wherein the highly radiopague first coil is formed from metal and the non-radiopague second coil is formed from a polymeric material.

5. A guidewire as defined in claim 4 wherein the polymeric second coil is of a larger diameter than the metal first coil.

6. A guidewire as defined in any of claims 1-3 wherein one of the coils is larger than the other, the larger coil being, at least at its surface, lubricious.

7. A guidewire as defined in claim 6 wherein the larger coil is formed from a low friction polymer.

* * * * *